United States Patent [19]

Gui et al.

[11] Patent Number: 5,759,950

[45] Date of Patent: Jun. 2, 1998

[54] CATALYST SUPPORTED WITH NOBLE METAL(S) FOR THE ISOMERIZATION OF ALKYLAROMATICS

[75] Inventors: Shouxi Gui; Yuzhi Hao; Lizhi Zhou; Zhenhua Jing; Yingbin Qiao; Haohui Gu; Yanqing Li; Baoyu Cheng; Jinshui Wang, all of Beijing, China

[73] Assignees: China Petrochemical Corporation; Research Institute of Petroleum Processing Sinopec, both of Beijing, China

[21] Appl. No.: 597,161

[22] Filed: Feb. 6, 1996

[30] Foreign Application Priority Data

Jun. 10, 1995 [CN] China ................................. 95116460.0
Jun. 10, 1995 [CN] China ................................. 95116461.9

[51] Int. Cl.$^6$ .......................... B01J 21/12; B01J 23/42; B01J 23/44

[52] U.S. Cl. ................. 502/339; 502/325; 502/334; 502/355; 502/77; 502/78

[58] Field of Search ........................ 502/339, 334, 502/325, 355, 78, 77

[56] References Cited

U.S. PATENT DOCUMENTS

| 3,637,881 | 1/1972 | Williams | 260/668 A |
|---|---|---|---|
| 3,767,721 | 10/1973 | Sonoda | 260/668 A |
| 4,100,262 | 7/1978 | Pelrine | 423/329 |
| 4,357,233 | 11/1982 | Dwyer et al. | 208/109 |
| 4,428,819 | 1/1984 | Shu et al. | 208/46 |
| 4,467,129 | 8/1984 | Iwayama et al. | 585/481 |
| 4,694,114 | 9/1987 | Chu et al. | 585/481 |

FOREIGN PATENT DOCUMENTS

| 85 1 00218B | 3/1987 | China . | |
|---|---|---|---|
| 1018986 | 1/1989 | China | B01J 29/22 |
| 1018986B | 11/1992 | China . | |
| 0 015 702 | 9/1980 | European Pat. Off. . | |
| 0 018 090 | 10/1980 | European Pat. Off. . | |
| 0 390 058 A1 | 10/1990 | European Pat. Off. . | |
| 0458378 | 3/1991 | European Pat. Off. | B01J 29/06 |
| 0 458 378 A2 | 11/1991 | European Pat. Off. . | |
| 0 065 401 | 11/1992 | European Pat. Off. . | |
| 28 23 567 | 12/1978 | Germany . | |

Primary Examiner—Glenn Caldarola
Assistant Examiner—Alexander G. Ghyka
Attorney, Agent, or Firm—Burns, Doane, Swecker & Mathis LLP

[57] ABSTRACT

A catalyst supported with noble metal(s) for the isomerization of alkylaromatics consists of (1) 0.1–0.4 wt % of Pt or (2) 0.1–0.4 wt % of Pt or 0.2–0.8 wt % of Pd, 0.01–0.20 wt % of Re and 0.05–0.50 wt % of Sn as active component, and 10–60 wt % of a zeolite with MOR structure, 0–15 wt % of ZSM-5 zeolite and 40–80 wt % of alumina as support.

28 Claims, No Drawings

5,759,950

1

CATALYST SUPPORTED WITH NOBLE METAL(S) FOR THE ISOMERIZATION OF ALKYLAROMATICS

FIELD OF THE INVENTION

This invention relates to a catalyst supported with Group VIII noble metal(s) suitable for the isomerization of alkylaromatics and a process for preparing the same. More particularly, this invention relates to a catalyst consisting of a support containing a zeolite and alumina, and an active component containing Pt, and a process for preparing the same.

BACKGROUND OF THE INVENTION $C_8$ aromatics is usually referred to a mixture of para-xylene(PX), meta-xylene(MX), ortho-xylene(OX) and ethyl benzene(EB), and can be obtained from catalytic reforming or petroleum cracking. PX and OX can be used in many fields, for example, they can be used as starting materials for synthesizing polyesters and benzoic anhydride. PX and OX can be separated from mixtures of $C_8$ aromatics, and the raffinate may be converted to a near-equilibrium mixture of PX, MX and OX by isomerization process. This is an effective method for increasing PX yield.

In order to increase the isomerization conversion of $C_8$ aromatics and the conversion of ethyl benzene to xylene, many isomerization processes have been developed, for example, OCTAFINING method (Engelhard Co.), ISOMAR method (UOP Co.), ISOLENE-II method (Toray Co.) etc., wherein dual-function catalysts supported with noble metals are used, which are disclosed in U.S. Pat. Nos. 3,637,881; 3,767,721; DE.Pat.No. 2,823,567. Recently the commercial catalyst (product from EMC and UOP Co.) most commonly used in isomerization is a dual-function catalyst supported with noble metal(s). The compositions of these catalysts are H-mordenite-alumina supported with Pt and/or Pd, the catalysts are mainly prepared by ion exchanging a Na-mordenite powder with an ammonium salt solution or dilute hydrochloric acid to remove a part of sodium cations, then drying and calcining to give a H-mordenite from which sodium cations are removed to some degree, then, mixing with a alumina supported with noble metals Pt or Pd and a binder, and finally molding to give a catalyst. In this process, the yield is relatively low, and the energy consumption is relatively high.

EP 458,378, discloses a catalyst for the isomerization of $C_8$ aromatics, comprising Pt as active component, and a H-mordenite containing 2–3 wt % of alkali metal cations and a binder selected from trihydrate-alumina or gamma-alumina as support. The catalyst is prepared by ion exchanging a mordenite to H-mordenite followed by mixing with a binder or alternatively by mixing mordenite with a binder followed by molding and ion exchanging to give a H-zeolite, and finally impregnating with Pt, then calcining and reducing.

Our patent of CN 89100145X also discloses a catalyst supported with noble metals for the isomerization of $C_8$ alkylaromatics, comprising a H-Na-mordenite and alumina as support.

Since ZSM series zeolites were invented, a lot of isomerization catalysts containing this kind of zeolite have been developed, such as those containing ZSM-5 zeolite (U.S. Pat. No. 4,100,262), containing ZSM-25 zeolite (EP 15702), containing ZSM-39 zeolite (U.S. Pat. No. 4,357,233), containing a zeolite with a crystalline phase intermediate of ZSM 5/ZSM 11 (EP 18,090; EP 65,401), containing a zeolite with a silica to alumina molar ratio of greater than 12 and a constraint index of 1 to 12 (U.S. Pat. No. 4,428,819), etc.

U.S. Pat. No. 4,694,114 discloses a catalyst for the isomerization of alkylaromatics, comprising a ZSM-23 and alumina as support, which is supported with a hydrogenation-dehydrogenation metals e.g. Pt, Pd or Ni etc.

EP 390,058 discloses a catalyst for the isomerization of $C_8$-aromatics, comprising a ZSM zeolite with a silica to alumina molar ratio of 30–200 and alumina as support, which is supported with Pt-Sn and/or In.

U.S. Pat No. 4,467,129 discloses a catalyst containing a dual zeolite system for the isomerization of $C_8$ alkylaromatics, comprising an acidic mordenite and a specific acidic zeolite( e.g.ZSM-5, -8, -11) as support, and other components such as inert alumina, which is supported with a metal component selected from Re, Mo, W and V. The catalyst is prepared by homogeneously mixing the dual zeolite system with a diluent (e.g. alumina), then adding a binder (e.g. alumina gel), followed by kneading and molding by extrusion, and then drying and calcining, then exchanging with an ammonium salt solution to a definite sodium content followed by calcining, and finally impregnating with metal component and activating.

On the basis of the prior art, an object of the present invention is to provide two kinds of catalysts possessing excellent properties for the isomerization of alkylaromatics by which an isomerization process can give a near-equilibrium mixture of para-, meta- and ortho-alkylaromatics.

Another object of the present invention is to provide a process for preparring the catalyst.

Other objects of the present invention can be apparent from the specification including the following Examples.

SUMMARY OF THE INVENTION

The catalyst provided in this invention consists of (1) 0.1–0.4 wt % of Pt or (2) 0.1–0.4 wt % of Pt or 0.2–0.8 wt % of Pd, 0.01–0.20 wt % of Re and 0.05–0.50 wt % of Sn as active component, and 10–60 wt % of a zeolite with MOR structure, 0–15 wt % of ZSM-5 zeolite and 40–80 wt % of alumina as support. Said catalyst is prepared by mixing a Na-zeolite with alumina or its precursor, then extruding and then calcining to give a support; ion exchanging said support with an ammonium salt solution until the exchanged sodium cation content reaches 30–95%, then drying and impregnating with a solution of active component metal compounds, and finally activating.

DETAILED DESCRIPTION OF THE INVENTION

In an embodiment of the present invention, the catalyst is supported with 0.1–0.4 wt % of Pt as active component. In another embodiment of the present invention, the catalyst is supported with three kinds of metal elements as active component, i.e. Pt or Pd, Re and Sn, the contents of them (based on the weight of the catalyst ) are as follows: 0.1–0.4 wt % of Pt or 0.2–0.8 wt % of Pd, 0.01–0.20 wt % of Re and 0.05–0.50 wt % of Sn. The support in these two kinds of catalyst is a complex support consisting of a zeolite and alumina, wherein the zeolite may be a zeolite with MOR structure or a dual zeolite system consisting of a zeolite with MOR structure and ZSM-5 zeolite. The contents of zeolite with MOR structure, ZSM-5 zeolite and alumina are 10–60%, 0–15% and 40–80%, respectively, by weight of the support.

Said zeolite with MOR structure has the X-ray diffraction pattern shown in Table 1, an anhydrous formula as follows (in terms of molar ratios of oxides): 1.0–7.0 Na$_2$O. Al$_2$O$_3$.10–60 SiO$_2$, and a adsorption weight ratio of n-hexane to cyclohexane of less than 1.0. Preferably, the zeolite with MOR structure used in the present catalyst has a silica to alumina molar ratio of 10–30, and a crystal size of less than 1 μm. The zeolite with MOR structure is prepared by using amorphous aluminosilicate micro sphere, sodium hydroxide and water as starting materials, and using sodium chloride or sodium chloride triethanolamine as templating agent. Detailed description of said zeolite and a process for preparing the same is disclosed in the Chinese Patent Application No. 95116456.2.

Preferably, the ZSM-5 zeolite used in the present catalyst has a silica to alumina molar ratio of 100–500, and a crystal size of less than 1 μm.

TABLE 1

| d-spacing (Å) | I/I$_0$ | |
|---|---|---|
| 13.74 ± 0.10 | W-VW | |
| 9.13 ± 0.10 | M-W | |
| 6.60 ± 0.10 | W | |
| 6.40 ± 0.06 | W-VW | |
| 5.81 ± 0.03 | VW | |
| 4.53 ± 0.03 | W | |
| 3.99 ± 0.03 | S | |
| 3.75 ± 0.03 | VW | |
| 3.47 ± 0.03 | VS | |
| 3.42 ± 0.03 | W | } twin peaks |
| 3.39 ± 0.03 | M | |
| 3.25 ± 0.03 | M-W | } not fully resolved |
| 3.21 ± 0.03 | M | | wherein the abbreviations of intensities are designated as follows:

very strong, (VS)=80–100%
strong (S)=60–80%
medium (M)=40–60%
weak (W)=20–40%
very weak (VW)<20%

The alumina used in the complex support may be eta-alumina or gamma-alumina, preferably gamma-alumina obtained from hydrolysis of alkoxylaluminium, especially gamma-Al$_2$O$_3$ with high purity obtained from hydrolysis of alkoxylaluminium in which the alkyl group is a lower alkyl group, which is prepared as disclosed in CN 85100218.8.

The process for preparing the present catalyst comprises the following four steps:

1. Preparation of support: extruding a mixture of a Na-zeolite and alumina or its precursor, and then calcining to give a support. In particular, mixing a Na-zeolite with MOR structure, or a mixture of said Na-zeolite and ZSM-5 zeolite with alumina or its precursor at a predetermined proportion, then adding dilute nitric acid as an adhesive to facilitate extruding, the concentration of dilute nitric acid is generally 1–5 wt %, preferably 1.5–3.0 wt %. The weight ratio of dilute nitric acid added to the above mentioned mixture is 1:0.25–0.60, preferably 1:0.35–0.45. Then mixing and kneading, extruding, drying and calcining in air at 470°–650° C. preferably at 500°–600° C. for 2–8 hours, preferably for 3–6 hours.

2. Ammonium cation exchange of the support: Ion exchanging the support with an ammonium salt solution until the exchanged sodium cation content in said zeolite reaches 30–95%. In particular, ion exchanging the support obtained above several times with a 0.1–0.8N, preferably 0.2–0.5N solution of an ammonium salt selected from ammonium chloride, ammonium nitrate and ammonium sulfate at a temperature between room temperature and 120° C., preferably 85°–100° C., for 1–6 hours, preferably 1–3 hours each time, until the exchanged sodium cation content reaches 30–95%, preferably 55–85%, then filtrating and washing free Na$^+$.

3. Impregnation of the active component: impregnating the dried support with a solution of metal compounds as active component. In particular, impregnating the ammonium exchanged support at room temperature and at a liquid to solid weight ratio of 1–3 with (1) a solution of platinum compound or (2) a solution of Pt or Pd, Re and Sn compounds for 8–60 hours, preferably 12–36 hours, then filtrating and drying. Said metal compounds refer to soluble compounds usually used in impregnation, for example, chloroplatinic acid, palladium chloride, perrhenic acid or soluble tin salt (e.g. SnCl$_2$). The Pt in the catalyst of the first embodiment and Sn in the catalyst of the second embodiment may be pre-impregnated in alumina, then mixed with zeolite.

4. Activation of catalyst: The activation process is carried out in air at 400°–600° C., preferably 450°–550° C. for 1–10 hours, preferably 3–6 hours.

Compared with the catalysts of the prior art, the two catalysts provided in the present invention utilize the specific zeolite with MOR structure, and the complex support with a special composition and match the active metal components, thus bringing the activity, selectivity and stability of a isomerization reaction to a higher level, and achieving a near-equilibrium mixture of para-, meta- and ortho-alkylaromatics in a isomerization process. These two series of catalysts can suitably be used not only in the isomerization of C$_8$ aromatics containing 10–40 wt % of ethylbenzene but also in the isomerication of C$_9$ and C$_{10}$ aromatics to give 1, 3, 5-trimethylbenzene or para-diethylbenzene.

The process for preparing the catalyst provided in the present invention not only brings the function of active component into full play, but also optimizes the synergetic effect between the active component and the support. This preparation process also decreases the powder pollution from the support materials and the loss of zeolite during ion exchanging process, and increases the yield of zeolite and exchanging efficiency with the ammonium salt.

EXAMPLES

The following examples are given in order to further illustrate the present invention without limiting the same.

In the examples, the zeolite with MOR structure is synthesized according to the method disclosed in CN 95116456.2, while ZSM-5 zeolite and gamma-alumina are commercial products.

The symbols used in the example are explained as follows:

<C$_7^{N+P}$-- cycloalkane and alkane with less than seven carbon atoms;

C$_8^{N+P}$-- cycloalkane and alkane with eight carbon atoms;

B -- benzene;

T -- toluene;

EB -- ethylbenzene;

PX -- para-xylene;

MX -- meta-xylene;

OX -- ortho-xylene.

In the examples PX/ΣX, yield of $C_8$ hydrocarbon and conversion of EB are calculated as follows:

PX/ΣX=[concentration of PX in product/concentration of (PX+MX+OX) in product]×100%

Yield of $C_8$ hydrocarbon=[concentration of Σ $C_8$ in product/concentration of $\Sigma C_8$ in feedstock]×100%, wherein concentration of $\Sigma C_8$=concentration of (PX+MX+OX+EB+$C_8^{N+P}$)

Conversion of EB=[(concentration of EB in feedstock-concentration of EB in product)/concentration of EB in feedstock]×100%

Comparative Example 1

Preparation of comparative catalyst sample of Pt-Re/mordenite-gamma-alumina:

25 g of mordenite with a silica to alumina molar ratio of 12.5 (based on dry weight) was mixed with 75 g of gamma-alumina, then added 40 ml of 2 wt % of nitric acid solution. The mixture was mixed and kneaded, molded by extrusion then dried at 110°–120° C. for 1 hours, and calcinated in air at 550° C. for 4 hours to give a support. 10 g of the support prepared above was exchanged with 25 ml of 2 wt % of ammonium chloride solution at 90±10° C. for 2 hours, washed the free $Na^+$, and dried. The exchanged $Na^+$content was 75%, calculated from the $Na^+$content in the zeolite before and after ion exchange.

The ammonium cation exchanged support prepared above was impregnated with a solution of chloroplatinic acid and perrhenic acid until it was supported with 0.4 wt % of Pt and 0.1 wt % of Re. The support was dried and activated in air at 500° C. for 4 hours.

The comparative catalyst thus obtained was designated as Sample A.

Comparative Example 2

Preparation of comparative catalyst Sample of Pt-Sn/mordenite-gamma-alumina:

The comparative catalyst Sample was prepared in the same manner as described in Comparative Example 1, except that the support was supported with 0.4 wt % of Pt and 0.2 wt % of Sn.

The comparative catalyst thus obtained was designated as Sample B.

Comparative Example 3

Preparation of comparative catalyst sample of Pt/mordenite-gamma-alumina:

The comparative catalyst sample was prepared in the same manner and the same conditions as described in Comparative Example 1, except that the support was supported with 0.4 wt % of Pt.

The comparative catalyst thus obtained was designated as Sample A'.

Example 1

Preparation of the catalyst of the present invention:

The catalyst samples B', C', D', E' and F' with different compositions of the first embodiment and the catalyst samples C, D, E, F, G, H, I and J with different compositions of the second embodiment were prepared in the same manner as described in Comparative Example 1, Except for starting from a zeolite with MOR structure with a silica to alumina molar ratio of 12.3 and ZSM-5 zeolite with a silica to alumina molar ratio of 150. The compositions of all these catalyst and the catalysts in Comparative Examples 1, 2 and 3 were listed in Table 2 and Table 3.

TABLE 2

| catalyst | Composition (wt %) | | | | |
|---|---|---|---|---|---|
| | Pt | mordenite | MOR zeolite | ZSM-5 | gamma-$Al_2O_3$ |
| A' | 0.40 | 33 | 0 | 0 | 67 |
| B' | 0.35 | 0 | 33 | 0 | 67 |
| C' | 0.35 | 0 | 32 | 3 | 65 |
| D' | 0.25 | 0 | 25 | 5 | 70 |
| E' | 0.35 | 0 | 33* | 0 | 67 |
| F' | 0.35 | 0 | 32 | 3** | 65 |

*with a silica to alumina molar ratio of 20;
**with a silica to alumina molar ratio of 300.

TABLE 3

| catalyst | Pt | Re | Sn | mordenite | MOR zeolite | ZSM-5 | gamma-$Al_2O_3$ |
|---|---|---|---|---|---|---|---|
| A | 0.40 | 0.10 | 0.00 | 33 | 0 | 0 | 67 |
| B | 0.40 | 0.00 | 0.20 | 33 | 0 | 0 | 67 |
| C | 0.25 | 0.05 | 0.30 | 0 | 33 | 0 | 67 |
| D | 0.20 | 0.10 | 0.10 | 0 | 33 | 0 | 67 |
| E | 0.25 | 0.05 | 0.30 | 0 | 32 | 3 | 65 |
| F | 0.25 | 0.05 | 0.30 | 0 | 33 | 0 | 67*** |
| G | 0.25 | 0.05 | 0.30 | 0 | 32 | 3 | 65*** |
| H | 0.25 | 0.05 | 0.30 | 0 | 25 | 5 | 70*** |
| I | 0.25 | 0.05 | 0.30 | 0 | 33* | 0 | 67 |
| J | 0.25 | 0.05 | 0.30 | 0 | 32 | 3** | 65 |

*with a silica to alumina molar ratio of 20;
**with a silica to alumina molar ratio of 300;
***Sn component was pre-impregnated in gamma-$Al_2O_3$.

Example 2

This example illustrates that the catalyst provided in the present invention possesses excellent properties for the isomerization of xylene.

The Comparative catalysts and the catalysts provided in the present invention were evaluated for their activities in the isomerization of $C_8$ aromatics in a 10 ml micro-reactor. The reaction conditions were as follows: 380° C., 0.8 MPa, a hydrogen-to-Hydrocarbon volume ratio of 1000/1, and $H_2$ was passed once-through. The amount of catalyst charged was 5 g. The composition of the feed was as follows (wt %):

$<C_7^{N+P}$: 0.16; $C_8^{N+P}$: 6.45; B: 0.53; T: 0.65; EB: 12.24; PX: 0.0; MX: 53.70; OX: 26.28.

The evaluation results of the catalysts of the first embodiment at a weight hourly space velocity of 3.5 $h^{-1}$ was listed in Table 4 (wt %). The evaluation results of the catalysts of the second embodiment at a weight hourly space velocity of 4.0 $h^1$ was listed in Table 5 (wt %).

TABLE 4

| catalyst | PX conc. | PX/ΣX | yield of $C_8$ hydrocarbon | EB Conv. |
|---|---|---|---|---|
| A' | 17.0 | 21.2 | 96.5 | 12.0 |
| B' | 17.5 | 22.0 | 97.0 | 17.0 |
| C' | 17.5 | 22.2 | 97.4 | 17.7 |
| D' | 17.0 | 21.9 | 97.0 | 18.5 |
| E' | 17.5 | 22.0 | 96.8 | 23.0 |
| F' | 17.2 | 22.0 | 97.0 | 19.4 |

TABLE 5

| catalyst | PX conc. | PX/ΣX | yield of $C_8$ hydrocarbon | EB Conv. |
|---|---|---|---|---|
| A | 17.5 | 22.0 | 96.5 | 20.0 |
| B | 17.0 | 21.5 | 96.8 | 25.0 |
| C | 18.2 | 22.7 | 97.5 | 27.0 |
| D | 18.3 | 22.8 | 97.4 | 23.5 |
| E | 18.7 | 23.1 | 97.8 | 30.0 |
| F | 18.7 | 22.9 | 97.7 | 25.4 |
| G | 19.0 | 23.3 | 98.0 | 25.1 |
| H | 18.2 | 22.9 | 97.2 | 35.6 |
| I | 17.0 | 22.1 | 96.7 | 33.4 |
| J | 18.4 | 22.7 | 98.0 | 24.5 |

Example 3

This example illustrates that the catalyst provided in the present invention is suitable for isomerization under various process conditions.

Catalyst C' of the first embodiment of the present invention and catalyst E of the second embodiment of the present invention were tested in the same reactor and in the same amount of catalyst and feed as described in Example 2 under various process conditions. Hydrogen was also passed once-through.

The results of catalyst C' was listed in Table 6, while the results of catalyst E was listed in Table 7.

TABLE 6

| Process Condition | | | | Reaction Result, wt % | | | |
|---|---|---|---|---|---|---|---|
| Tempt. | WHSV | $H_2$/HC | Press. | | | | |
| °C. | $h^{-1}$ | (v/v) | MPa | PX Conc. | PX/ΣX | yield of $C_8$ hydrocarbon | EB Conv. |
| 390 | 3.5 | 1000/1 | 0.6 | 16.5 | 21.5 | 97.4 | 11.0 |
| 390 | 3.5 | 1000/1 | 1.8 | 17.2 | 21.7 | 95.5 | 30.0 |
| 440 | 3.5 | 1000/1 | 0.8 | 17.5 | 22.1 | 95.8 | 27.0 |
| 380 | 2.5 | 1000/1 | 0.6 | 18.1 | 22.2 | 96.0 | 17.5 |
| 380 | 3.0 | 1000/1 | 0.8 | 17.9 | 22.1 | 97.1 | 18.0 |
| 400 | 10.0 | 1000/1 | 0.9 | 16.0 | 21.0 | 98.2 | 10.2 |
| 380 | 3.5 | 1500/1 | 0.7 | 17.0 | 22.0 | 97.6 | 15.0 |
| 380 | 3.5 | 700/1 | 0.7 | 17.3 | 22.1 | 97.3 | 16.0 |

TABLE 7

| Process Condition | | | | Reaction Result, wt % | | | |
|---|---|---|---|---|---|---|---|
| Tempt. | WHSV | $H_2$/HC | Press. | | | | |
| °C. | $h^{-1}$ | (v/v) | MPa | PX Conc. | PX/ΣX | yield of $C_8$ hydrocarbon | EB Conv. |
| 390 | 4.0 | 1000/1 | 0.6 | 17.0 | 21.9 | 98.4 | 13.0 |
| 390 | 4.0 | 1000/1 | 1.8 | 18.2 | 22.0 | 96.5 | 30.0 |
| 440 | 4.0 | 1000/1 | 0.8 | 18.5 | 23.1 | 94.8 | 27.0 |
| 380 | 2.5 | 1000/1 | 0.6 | 19.1 | 23.2 | 96.3 | 17.5 |
| 380 | 4.0 | 1000/1 | 0.8 | 18.9 | 23.1 | 98.3 | 18.0 |
| 400 | 10.0 | 1000/1 | 0.9 | 16.2 | 21.0 | 98.5 | 12.2 |
| 380 | 4.0 | 1500/1 | 0.7 | 18.0 | 23.0 | 97.9 | 15.0 |
| 380 | 4.0 | 700/1 | 0.7 | 18.3 | 23.0 | 97.6 | 17.0 |

Example 4

This example illustrates that the catalyst provided in the present invention is suitable for the isomerization of $C_8$ aromatics with different contents of ethylbenzene.

The isomerization reaction result of catalyst C' at a weight hourly space velocity of 3.5 $h^{-1}$ was listed in Table 8, and the isomerization reaction result of catalyst E at a weight hourly space velocity of 4.0 $h^{-1}$ was listed in Table 9. Two kinds of $C_8$ aromatic feed with different contents of ethylbenzene 22.62 wt % and 11.25 wt %) was isomerized using catalyst C' of the first embodiment of the present invention and catalyst E of the second embodiment of the present invention in the same reactor and under the same operation conditions and in the same amount of catalyst as described in Example 2, respectively.

TABLE 8

| | Feed composition, wt % | | Product composition, wt % | |
|---|---|---|---|---|
| | I | II | I | II |
| $<C_7^{N+P}$ | 0.028 | 0.036 | | |
| $C_8^{N+P}$ | 10.30 | 12.62 | | |
| B | 0.34 | 0.45 | | |
| T | 1.20 | 1.38 | | |
| EB | 22.62 | 11.25 | 16.50 | 9.20 |
| PX | 2.44 | 2.89 | | |
| MX | 42.67 | 48.87 | | |
| OX | 20.40 | 22.51 | | |
| $C_8$ hydrocarbon | 98.43 | 98.13 | | |
| PX/ΣX | | | 21.71 | 22.08 |
| Yield of $C_8$ hydrocarbon | | | 95.56 | 96.04 |
| EB Conv. | | | 27.06 | 18.22 |

TABLE 9

| | Feed composition, wt % | | Product composition, wt % | |
|---|---|---|---|---|
| | I | II | I | II |
| <$C_7^{N+P}$ | 0.028 | 0.036 | | |
| $C_8^{N+P}$ | 10.30 | 12.62 | | |
| B | 0.34 | 0.45 | | |
| T | 1.20 | 1.38 | | |
| EB | 22.62 | 11.25 | 15.58 | 8.96 |
| PX | 2.44 | 2.89 | | |
| MX | 42.67 | 48.87 | | |
| OX | 20.40 | 22.51 | | |
| $C_8$ hydrocarbon | 98.43 | 98.13 | | |
| PX/ΣX | | | 22.01 | 22.28 |
| Yield of $C_8$ hydrocarbon | | | 96.96 | 97.04 |
| EB Conv. | | | 31.11 | 21.40 |

Example 5

This example illustrates that the catalyst provided in the present invention possesses good stability for isomerization.

Catalyst C' of the first embodiment and catalyst E of the second embodiment were tested for their stability in a 30 ml bench reactor under the conditions of 380°–383° C., a hydrogen-to-Hydrocarbon ratio (v/v) of 1000:1, a pressure of 0.8–0.9MPa and a amount of catalyst of 22 ml.

The product composition with catalyst C' after running at a weight hourly space velocity of 3.5 h$^{-1}$ for 1000 hours was as follows (wt %):
$C_8^{N+P}$: 7.19; B: 0.33; T: 0.96; EB: 10.51; PX: 17.36; Mx: 43.85; OX: 17.36, PX/ΣX: 22.09; Yield of $C_8$ hydrocarbon: 97.56: Conversion of EB: 15.38. The coke on the catalyst sample after running for 1000 hours was only 1.47 wt %.

The product composition with catalyst E after running at a weight hourly space velocity of 4.0 h$^{-1}$ for 1000 hours was as follows (wt %):
$C_8^{N+P}$: 8.15; B: 0.33; T: 0.96; EB: 9.80; PX: 18.36; MX: 42.05; OX: 18.36, PX/ΣX: 23.23; Yield of $C_8$ hydrocarbon: 97.80: Conversion of EB: 19.93. The coke on the catalyst sample after funning for 1000 hours was only 0.70 wt %.

Example 6

This example illustrates that the catalyst provided in the present invention is also suitable for the isomerization of $C_9$ aromatics. Trimethylbenzene feed was isomerized in a 10 ml micro reactor under the conditions of 430° C., 0.8 MPa, a liquid hourly space velocity of 3.1 h$^{-1}$ and a hydrogen-to-Hydrocarbon ratio (v/v) of 1000:1 using catalyst C' and E, respectively. The reaction results were listed in Table 10.

TABLE 10

| | Feed composition, wt % | Product composition, wt % | |
|---|---|---|---|
| | | Sample C' | Sample E |
| p-, m- and o- xylene | 0.03 | 6.00 | 6.10 |
| 1,3,5-trimethylbenzene | 0.45 | 19.09 | 19.69 |
| 1,2,5-trimethylbenzene | 99.12 | 60.03 | 59.03 |
| 1,2,3-trimethylbenzene | — | 8.02 | 8.42 |
| other $C_9$ aromatics | 0.37 | 0.20 | 0.21 |
| tetramethylbenzene | — | 5.0 | 4.9 |
| others | 0.03 | 1.66 | 1.65 |

Example 7

This example illustrates that the catalyst provided in the present invention is likewise suitable for the isomerization of $C_{10}$ aromatics.

Diethylbenzene feedstock was isomerized in a 10 ml micro-reactor under the conditions of 370° C., 0.7 MPa, a liquid hourly space velocity of 3.0 h$^{-1}$ and a hydrogen-to-hydrocarbon ratio (v/v) of 1500:1 using catalyst C' and E, respectively. The reaction results were listed in Table 11.

TABLE 11

| | Feed composition, wt % | Product composition, wt % | |
|---|---|---|---|
| | | Sample C' | Sample E |
| Nonaromatics | 0.03 | 7.91 | 8.91 |
| $C_8$–$C_{10}$ aromatics* | 6.16 | 7.03 | 6.63 |
| m-diethylbenzene | 79.82 | 51.42 | 50.42 |
| p-diethylbenzene | 9.20 | 21.0 | 21.30 |
| o-diethylbenzene | 3.97 | 5.46 | 6.16 |
| >$C_{10}$ aromatics | 0.82 | 6.08 | 6.58 |
| Total diethylbenzene | 92.99 | 77.88 | 77.88 |
| p-diethylbenzene/total diethylbenzene | | 26.96 | 27.35 |
| diethylbenzene Conv. | | 83.74 | 83.74 |

*indicating that the $C_{10}$ aromatics do not comprise diethylbenzene.

What is claimed is:

1. A catalyst for the isomerization of alkylaromatics, comprising 0.1–0.4 wt % of Pt or 0.2–0.8 wt % of Pd, 0.01–0.20 wt % of Re and 0.05–0.50 wt % of Sn as active components, 10–60 wt % of a zeolite having an MOR structure which has a X-ray diffraction pattern as shown in Table 1 and 40–80 wt % of alumina as a support.

2. The catalyst of claim 1, further comprising ZSM-5 zeolite in an amount up to 15 wt %.

3. The catalyst of claim 1, wherein the zeolite with an MOR structure has an anhydrous formula in terms of molar ratios of the oxides, as follows:

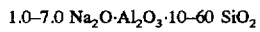

$$1.0\text{--}7.0\ Na_2O \cdot Al_2O_3 \cdot 10\text{--}60\ SiO_2$$

and an adsorption weight ratio of n-hexane to cyclohexane of less than 1.0.

4. The catalyst of claim 3, wherein the zeolite with an MOR structure has a silica to alumina molar ratio of 10–30, and a crystal size of less than 1 μm.

5. The catalyst of claim 1, wherein the ZSM-5 zeolite has a silica to alumina molar ratio of 100–500, and a crystal size of less than 1 μm.

6. The catalyst of claim 1, wherein the alumina is η-or γ-alumina.

7. The catalyst of claim 6, wherein the alumina is a high purity γ-alumina obtained by hydrolysis of alkoxyl aluminum.

8. A process for preparing the catalyst of claim 1, the process comprising the steps of:

(a) mixing a Na-zeolite having an MOR structure with alumina or a precursor thereof;

(b) extruding and calcining the resulting mixture thereby forming a support;

(c) ion-exchanging the support with an ammonium salt solution until the exchanged sodium cation content of the zeolite reaches 30–95%;

(d) drying and impregnating the support with a solution of one or more active metal compounds; and (e) activating the impregnated support thereby forming the catalyst.

9. The process of claim 8, wherein the support is prepared by:

mixing a Na-zeolite having an MOR structure, or a mixture of a Na-zeolite having an MOR structure and a ZSM-5 zeolite, with alumina or a precursor thereof:

kneading and extruding the resulting mixture; and drying and calcining the extrudate in air at 470°–650° C. for 2–8 hours.

10. The process of claim 8, wherein the ion-exchanging is carried out using a 0.1–0.8 N ammonium salt solution at a temperature between room temperature and 120° C. for 1–6 hours.

11. The process of claim 8, wherein the impregnating is carried out using a solution of chloroplatinic acid or palladium chloride, perrhenic acid and tin salt at a liquid to solid ratio of 1–3 at room temperature for 8–60 hours.

12. The process of claim 8, wherein the activating is carried out at a temperature of 400°–600° C. for 1–10 hours.

13. The process of claim 8, wherein prior to being mixed with the zeolite, the alumina is impregnated with the tin in the active components of the catalyst.

14. A catalyst for the isomerization of alkylaromatics, comprising (1) 0.1–0.4 wt % of Pt or (2) 0.1–0.4 wt % of Pt or 0.2–0.8 wt % of Pd, 0.01–0.20 wt % of Re and 0.05–0.50 wt % of Sn as active components, 10–60 wt % of a zeolite having an MOR structure which has an X-ray diffraction pattern as shown in Table 1 and 40–80 wt % of alumina as a support.

15. The catalyst of claim 14 further comprising ZSM-5 zeolite in an amount up to 15 wt %.

16. The catalyst of claim 14 wherein the zeolite with an MOR structure has an anhydrous formula in terms of molar ratios of the oxides, as follows:

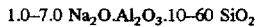

1.0–7.0 Na$_2$O.Al$_2$O$_3$.10–60 SiO$_2$ and an adsorption weight ratio of n-hexane to cyclohexane of less than 1.0.

17. The catalyst of claim 14, wherein the zeolite with an MOR structure has a silica to alumina molar ratio of 10–30, and a crystal size of less than 1 μm.

18. The catalyst of claim 14, wherein the ZSM-5 zeolite has a silica to alumina molar ratio of 100–500, and a crystal size of less than 1 μm.

19. The catalyst of claim 14, wherein the alumina is η-or γ-alumina.

20. The catalyst of claim 19, wherein the alumina is a high purity γ-alumina obtained by hydrolysis of alkoxyl aluminum.

21. A process for preparing the catalyst of claim 14, the process comprising the steps of:

(a) mixing a Na-zeolite having an MOR structure with alumina or a precursor thereof;

(b) extruding and calcining the resulting mixture thereby forming a support;

(c) ion-exchanging the support with an ammonium salt solution until the exchanged sodium cation content of the zeolite reaches 30–95%;

(d) drying and impregnating the support with a solution of one or more active metal compounds; and (e) activating the impregnated support thereby forming the catalyst.

22. The process of claim 21, wherein the support is prepared by:

mixing a Na-zeolite having an MOR structure, or a mixture of a Na-zeolite having an MOR structure and a ZSM-5 zeolite, with alumina or a precursor thereof;

kneading and extruding the resulting mixture; and drying and calcining the extrudate in air at 470°–650° C. for 2–8 hours.

23. The process of claim 21, wherein the ion-exchanging is carried out using a 0.1–0.8N ammonium salt solution at a temperature between room temperature and 120° C. for 1–6 hours.

24. The process of claim 21, wherein the impregnating is carried out using a solution of chloroplatinic acid, or a solution of chloroplatinic acid or palladium chloride, perrhenic acid and tin salt at a liquid to solid ratio of 1–3 at room temperature for 8–60 hours.

25. The process of claim 21 wherein the activating is carried out at a temperature of 400°–600° C. for 1–10 hours.

26. The process of claim 21 wherein prior to being mixed with the zeolite, the alumina is impregnated with the platinum in the active component (1) of the catalyst or the tin in the active components (2) of the catalyst.

27. A catalyst for the isomerization of alkylaromatics, comprising 0.1–0.4 wt % of Pt or 0.2–0.8 wt % of Pd, 0.01–0.20 wt % of Re and 0.05–0.50 wt % of Sn as active components, 10–60 wt % of a zeolite having an MOR structure and 40–80 wt % of alumina as a support.

28. The catalyst of claim 27 further comprising ZSM-5 zeolite in an amount up to 15 wt %.

* * * * *